(12) United States Patent
Park et al.

(10) Patent No.: US 11,865,017 B2
(45) Date of Patent: Jan. 9, 2024

(54) FINGER MOTION ASSIST APPARATUS

(71) Applicant: KOREA ADVANCED INSTITUTE OF SCIENCE AND TECHNOLOGY, Daejeon (KR)

(72) Inventors: Hyung-Soon Park, Daejeon (KR); Dong Hyun Kim, Daejeon (KR)

(73) Assignee: Korea Advanced Institute of Science And Technology, Daejeon (KR)

( * ) Notice: Subject to any disclaimer, the term of this patent is extended or adjusted under 35 U.S.C. 154(b) by 238 days.

(21) Appl. No.: 17/254,465

(22) PCT Filed: Dec. 18, 2020

(86) PCT No.: PCT/KR2020/018724
§ 371 (c)(1),
(2) Date: Dec. 21, 2020

(87) PCT Pub. No.: WO2022/131412
PCT Pub. Date: Jun. 23, 2022

(65) Prior Publication Data
US 2022/0401232 A1 Dec. 22, 2022

(51) Int. Cl.
*A61F 2/58* (2006.01)
*A61H 1/02* (2006.01)
*B25J 15/00* (2006.01)
*A61F 2/50* (2006.01)

(52) U.S. Cl.
CPC ............ *A61F 2/586* (2013.01); *A61H 1/0288* (2013.01); *B25J 15/0009* (2013.01); *A61F 2002/5093* (2013.01)

(58) Field of Classification Search
CPC ............ A61F 2/586; A61F 2002/5093; A61H 1/0288; B25J 15/0009
See application file for complete search history.

(56) References Cited

U.S. PATENT DOCUMENTS

2012/0150322 A1* 6/2012 Goldfarb ................. A61F 2/583
901/46
2015/0374575 A1* 12/2015 Kamper ................. A61F 5/013
601/40

FOREIGN PATENT DOCUMENTS

| JP | 2019-4996 A | 1/2019 |
|---|---|---|
| KR | 10-2005-0104974 A | 11/2005 |
| KR | 10-2017-0056722 A | 5/2017 |
| KR | 10-1932348 B1 | 12/2018 |
| KR | 10-2020-0003574 A | 1/2020 |

* cited by examiner

*Primary Examiner* — Bruce E Snow
(74) *Attorney, Agent, or Firm* — Maier & Maier, PLLC (57) ABSTRACT

An apparatus for assisting a finger motion, including a palm support installed to surround a part of a hand-back and a wrist; an extension assist unit secured at a first side thereof to a middle phalanx region of a finger and connected at a second side thereof to the palm support to assist extension of the finger through an elastic force between both ends; and a flexion assist unit comprising a distal phalange support mounted on an end of the finger, and a first flexion wire and a second flexion wire mounted on a part of the finger and assisting flexion of the finger on the basis of tensile force supplied from an outside.

13 Claims, 5 Drawing Sheets

——— Flexion tendon
--------- Intrinsic tendon
— — — Thumb flexion tendon
·········· Thumb opposition tendon

FIG.5

FINGER MOTION ASSIST APPARATUS

TECHNICAL FIELD

The present disclosure relates to an apparatus for assisting a finger motion.

BACKGROUND

Generally, since patients having hand paralysis after a cerebral stroke cannot spontaneously perform a joint movement, and suffer from various patterns and levels of ankylosis and stiffness, for example, motion assisting devices for performing effective rehabilitation with various hand movements are being developed.

For example, for a user having a deteriorated motor skill of the hand due to diseases or accidents or a user suffering from hand paralysis such as stiffness and ankylosis, the function of the hand is maintained or recovered by a rehabilitation exercise for flexing or extending the user's hand joint. To this end, a user performs a rehabilitation exercise with the aid of a physical therapist, or performs a rehabilitation exercise using exercise equipment.

Meanwhile, a conventional finger motion assisting device may generally transmit tension through a wire installed at an end of a finger, and a change in length of the wire may be caused by tension or friction. The change in length of the wire may subsequently lead to an error when a finger angle is controlled on the basis of the length of the wire.

Meanwhile, even when control is performed in consideration of the change, one wire may be inevitably loosened at the time of converting the flexion/extension of the joint, and a dead-zone in which the finger joint does not move may be formed.

Furthermore, there has been developed a motion assisting device capable of performing complicated finger movements, by mounting a driving source on each finger joint. However, this is problematic in that the device is excessively heavy, complicated in terms of control, and difficult to carry.

SUMMARY

In view of the above, the present disclosure provides an apparatus for assisting a finger motion.

Furthermore, the present disclosure provides an apparatus for assisting a finger motion, which compensates for non-linear characteristics caused by a change in length of a system due to friction and deformation, and can rapidly and accurately assist a user's finger.

However, the present disclosure is not limited to the above-mentioned objects, and other objects which are not mentioned will be clearly understood by those skilled in the art from the following description.

In accordance with an aspect of the present disclosure, there is provided An apparatus for assisting a finger motion, the apparatus comprises, a palm support installed to surround a part of a hand-back and a wrist; an extension assist unit secured at a first side thereof to a middle phalanx region of a finger and connected at a second side thereof to the palm support to assist extension of the finger through an elastic force between both ends; and a flexion assist unit comprising a distal phalange support mounted on an end of the finger, and a first flexion wire and a second flexion wire mounted on a part of the finger and assisting flexion of the finger on the basis of tensile force supplied from an outside.

Also the first flexion wire assists the flexion of a first joint or a second joint of all fingers, and the second flexion wire assists the extension of the first joint, and assists the flexion of the second joint.

Also the first joint is a proximal inter-phalangeal joint of the finger, and the second joint is a metacarpophalangeal joint of the finger.

Also the extension assist unit comprises a first fixing ring mounted on the middle phalanx region of the finger; a second fixing ring mounted on a proximal phalange region of the finger; and a first extension elastic member connected at a first end thereof to an outside part of the distal phalange support, and connected at a second end thereof to a part of the palm support coming into contact with the hand-back.

Also the first flexion wire is formed such that a first end thereof is secured to an inside part of the distal phalange support and a second end thereof passes through an inside of the finger and a part of the palm support coming into contact with the palm, and the second flexion wire is formed such that a first end thereof is secured to a part of the first extension elastic member passing through an outside of the middle phalanx region of the finger, and a second end thereof surrounds a circumference of the proximal phalange region of the finger obliquely inwards and then passes through a part of the palm support coming into contact with the palm.

Also the extension assist unit further comprises a second extension elastic member which is connected at a first end thereof to an outside part of the distal phalange support and is connected at a second end thereof to a part of the palm support coming into contact with the wrist, the first fixing ring is installed on all the fingers except for a thumb, the second fixing ring and the first extension elastic member are installed on all the fingers, and the second extension elastic member is installed on only the thumb.

Also the flexion assist unit further comprises a third flexion wire surrounding the metacarpophalangeal joint, the first flexion wire is installed on all the fingers, the second flexion wire is installed on only an index finger and a middle finger, the third flexion wire is installed on only the thumb, and is formed such that a first end thereof is secured to a wire holding device installed in the palm support and a second end thereof surrounds the metacarpophalangeal joint of the thumb and then passes through the wire holding device.

Also the palm support comprises a hand-back support mounted to surround the metacarpal region in the palm; a wrist support mounted to surround a wrist region in the palm; and a plurality of coupling buttons disposed along circumferences of the hand-back support and the wrist support to be spaced apart from each other, wherein the first extension elastic member or the second extension elastic member comprises a coupling hole that may be coupled to any one coupling button among the plurality of coupling buttons.

Also the extension assist unit is mounted on the thumb, the second fixing ring is installed on the proximal phalange region, the coupling hole of the first extension elastic member is coupled to any one coupling button among the plurality of coupling buttons formed on the hand-back support, and the coupling hole of the second extension elastic member is coupled to any one coupling button among the plurality of coupling buttons formed on the wrist support, and when the extension assist unit is mounted on fingers other than the thumb, the first fixing ring is installed on the middle phalanx region, the second fixing ring is installed on the proximal phalange region, and the coupling hole of the first extension elastic member is coupled to any one coupling button among the plurality of coupling buttons formed on the hand-back support.

Also the first flexion wire passes through an inside part of each of the first and second fixing rings mounted on the finger equipped with the flexion assist unit, and the second flexion wire passes through the inside part of the second fixing ring mounted on the finger equipped with the flexion assist unit.

Also the flexion assist unit is mounted on the thumb, the flexion assist unit further comprises a metacarpal support mounted to surround the metacarpal region of the thumb, and the first flexion wire or the second flexion wire is formed to pass through the palm support after passing through an inside part of the metacarpal support.

Also An apparatus for assisting a finger motion is further comprises a motion detection sensor mounted on the finger or the palm to measure movement of a hand; and a controller calculating tensile force of at least one of the first flexion wire, the second flexion wire, and the third flexion wire for the finger flexion on the basis of information measured by the motion detection sensor, and controlling an external device to provide the calculated tensile force to at least one of the first flexion wire, the second flexion wire, and the third flexion wire.

Also the motion detection sensor comprises an inertia sensor to detect inertia of the finger or the palm region or a bending detection sensor to detect a joint motion of a finger region.

A finger motion assisting apparatus in accordance with an embodiment of the present disclosure selectively combines one or more modules among an extension assist unit and a flexion assist unit depending on the symptoms and conditions of patients, thus effectively assisting the movement of the hand.

Furthermore, it is possible to passively or actively assist rehabilitation training for patients with a brain injury who suffer from hand paralysis after damage to a nervous system such as a cerebral stroke or cerebral palsy.

Furthermore, it is possible to naturally stretch the finger which is bent due to stiffness, using a passive type extension assist unit.

Furthermore, it is possible to perform the flexion or extension of the thumb as well as the opposition for rotating the thumb to the inside of the palm or the reposition for restoring the finger from the rotated state, using a first extension elastic member, a second extension elastic member, a first flexion wire, and a third flexion wire.

Furthermore, it is possible to individually control the angles of the metacarpophalangeal joint and the proximal joint of the index finger and the middle finger, using a first extension elastic member, a first flexion wire, and a second flexion wire.

Furthermore, since the tensile force of a first flexion wire or a second flexion wire for the finger flexion is calculated and the first flexion wire or the second flexion wire is controlled according to the calculated tensile force, torque is provided according to the individual angle control of the metacarpophalangeal joint and the proximal joint of the index finger and the middle finger. Thus, as the angle and the torque are simultaneously controlled, the first flexion wire or the second flexion wire showing nonlinear characteristics due to friction and deformation is compensated for, so that the finger flexion can be rapidly and accurately assisted.

DETAILED DESCRIPTION

Hereinafter, embodiments will be described in detail with reference to the accompanying drawings. The same reference numerals are used throughout the drawings to designate the same or similar components. In describing the embodiments of the present disclosure, the detailed descriptions of well-known functions or configurations will be omitted if it is determined that the detailed descriptions of well-known functions or configurations may unnecessarily make obscure the spirit of the present disclosure.

Further, in describing the embodiments of the present disclosure, the terms "first", "second", "A", "B", "(a)", "(b)", etc. may be used herein. These terms are only used to distinguish one component from another component. The nature, sequence, or order of corresponding components is not limited by these terms. It will be understood that when a component is referred to as being "coupled" or "connected" to another component, it can be directly coupled or connected to the other component or intervening components may be present therebetween.

The same terms are used to designate a component included in one embodiment and a component of another embodiment having a common function. Unless otherwise stated, the description of any one embodiment may be applied to other embodiments, and a duplicated description thereof will be omitted.

Figure 1:
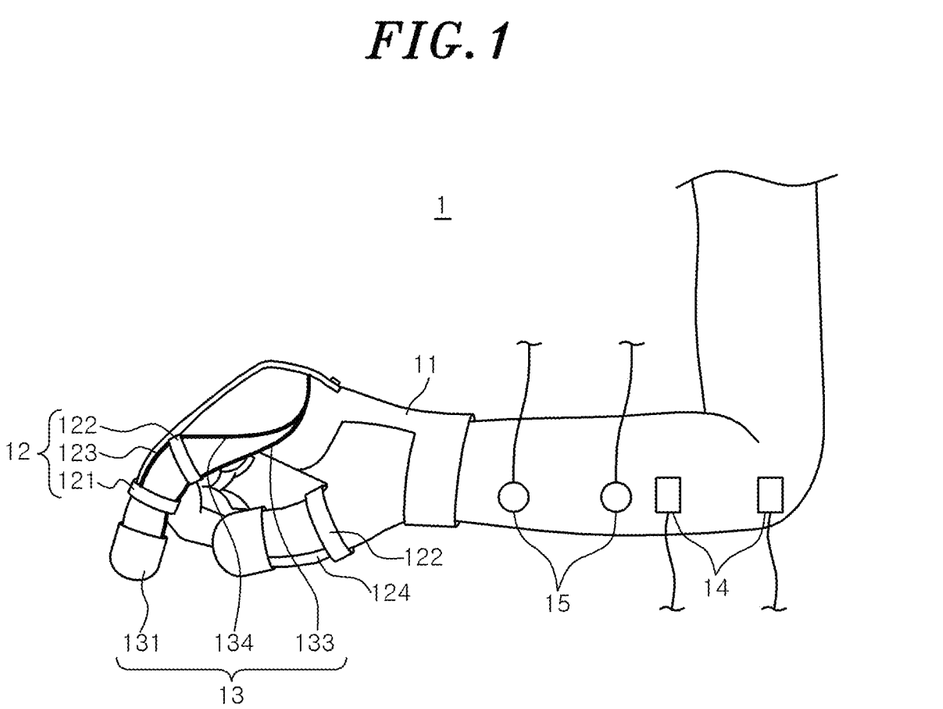
FIG. 1 describes a diagram illustrating a state in which a finger motion assisting apparatus in accordance with an embodiment is worn.
Figure 2:
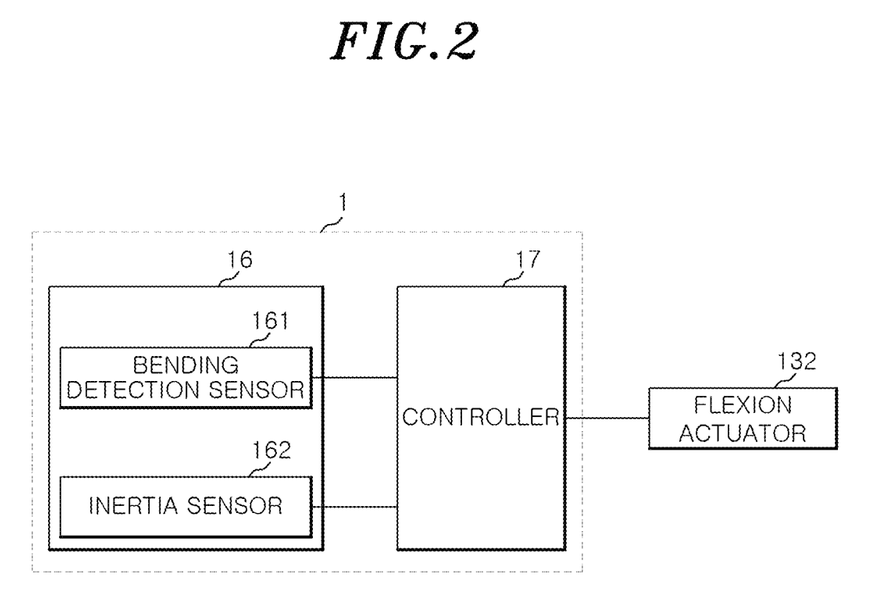
FIG. 2 depicts a block diagram of a finger motion assisting apparatus in accordance with an embodiment.
Figure 3:
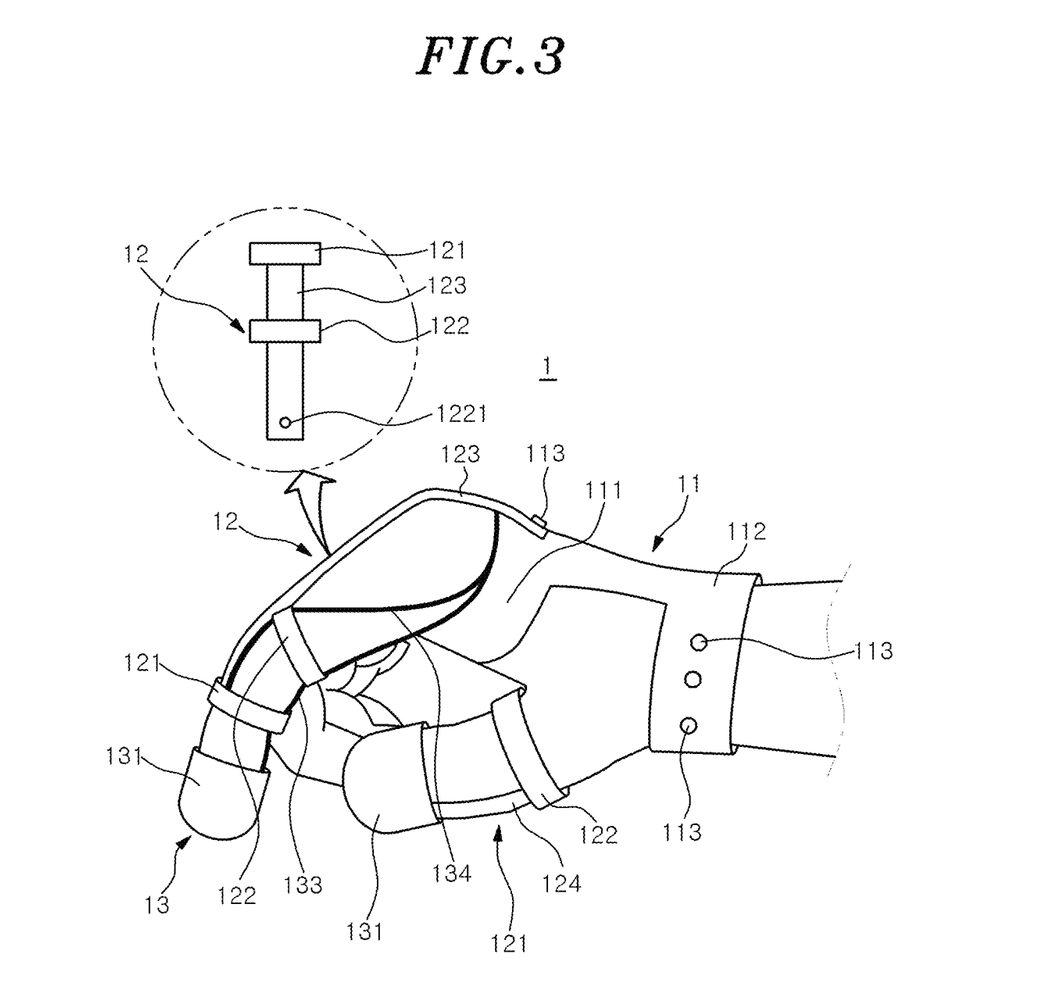
FIG. 3 represents a diagram illustrating an extension assist unit and a flexion assist unit in accordance with an embodiment.

FIG. 1 describes a diagram illustrating a state in which a finger motion assisting apparatus in accordance with an embodiment is worn, FIG. 2 depicts a block diagram of a finger motion assisting apparatus in accordance with an embodiment. and FIG. 3 represents a diagram illustrating an extension assist unit and a flexion assist unit in accordance with an embodiment.

Referring to FIGS. 1, 2 and 3, a finger motion assisting apparatus 1 in accordance with an embodiment may be worn on a hand having a deteriorated motor skill to assist the extension and flexion of the fingers.

Although it is described herein that the finger performs the extension or the flexion, the present disclosure is not limited thereto. In other words, it is to be understood that the extension or the flexion described herein is performed in the joint of the finger.

For example, the finger motion assisting apparatus 1 may include a palm support 11, an extension assist unit 12, a flexion assist unit 13, a motion detection sensor 16, a neural inhibition electrode 14, a muscle excitation electrode 15, and a controller 17.

The palm support 11 may be formed to surround at least a part of a user's wrist and palm. For example, the palm support 11 may be formed to surround a part of the carpal and the metacarpal constituting the wrist bone.

The extension assist unit 12 may be worn between the user's finger and the palm support 11 to apply an elastic force in a direction where the finger performs the extension.

The flexion assist unit 13 may be installed between the user's finger and the palm support 11 to allow the finger to perform the flexion.

The palm support 11, the extension assist unit 12, and the flexion assist unit 13 will be described below with reference to FIGS. 4 to 5.

The motion detection sensor 16 may be installed on the user's finger to measure the posture and movement of the hand including the finger.

For example, the motion detection sensor 16 may include a bending detection sensor 161 or an inertia sensor 162.

The bending detection sensor 161 may be installed on the joint of the user's finger to measure a bending degree. For example, the bending detection sensor 161 may be either a bending sensor which measures a bending degree or a stretchable sensor which detects a stretching degree caused by an external force.

For example, the bending detection sensor 161 may be installed in the palm support 11, the extension assist unit 12, or the flexion assist unit 13.

The inertia sensor 162 may be attached to the user's palm or finger, and may measure the inertial force of the hand including the finger according to the grip or grip releasing action of the finger or palm.

For example, the inertia sensor 162 may be installed in the palm support 11, the extension assist unit 12, or the flexion assist unit 13.

The neural inhibition electrode 14 may electrically inhibit nerves connected from the brain to connecting muscle used for the finger motion so as to inhibit the muscular motion of the finger, thus preventing the muscular contraction of the connecting muscle.

For example, the neural inhibition electrode 14 may be a pair of surface electrodes which are detachably attached to the skin near the nerve of the user's connecting muscle and are composed of a negative pole and a positive pole. For example, the negative pole may be attached to the user's elbow bone, while the positive pole may be attached to the user's wrist or forearm to interfere with a motor nerve signal transmitted to the median nerve and ulnar nerve of the arm. For example, the alternating current of a medium frequency may be applied to the neural inhibition electrode 14.

For example, since the neural inhibition electrode 14 may prevent the muscular contraction of the connecting muscle of the finger during the extension of the finger assisted through the extension assist unit 12, the bending, ankylosis, and stiffness of the finger may be inhibited, thus easily assisting the extension of the finger.

The muscle excitation electrode 15 may generate an electric signal for contracting the connecting muscle used to move the finger. In other words, the muscle excitation electrode may transmit a functional electrical stimulation for moving the muscle to the connecting muscle.

For example, the muscle excitation electrode 15 may be a pair of detachable surface electrodes which are attached to the user's skin and composed of the negative pole and the positive pole. For example, the muscle excitation electrode 15 may be attached to the forearm, and may be attached to the skin near the nerve connected to the connecting muscle. For example, the current of a low frequency may be applied to the muscle excitation electrode 15.

For example, the muscle excitation electrode 15 may contract the connecting muscle of the finger during the bending of the finger assisted through the flexion assist unit 13, thus assisting the bending of a corresponding finger.

Meanwhile, the neural inhibition electrode 14 and the muscle excitation electrode 15 may be formed to be connected to different channels provided in one electric stimulator.

The controller 17 may control the operation of the finger motion assisting apparatus 1.

For example, the controller 17 may operate the flexion actuator 132 which is an external device which is not included in the finger motion assisting apparatus 1 to perform the flexion of the finger wearing the flexion assist unit 13. For example, the controller 17 may apply a current to the neural inhibition electrode 14, thus inhibiting the connecting muscle of the finger from contracting. For example, the controller 17 may apply a current to the muscle excitation electrode 15, thus contracting the connecting muscle of the finger.

Meanwhile, although it is described that the flexion actuator 132 is included in the finger motion assisting apparatus 1, it may be not included in the finger motion assisting apparatus 1 without being limited thereto.

In an embodiment, when the flexion actuator 132 is included in the finger motion assisting apparatus 1, the flexion actuator 132 may be connected to second ends of a first flexion wire 133, a second flexion wire 134, and a third flexion wire 135, which are secured at first ends thereof to a distal phalange support 131, thus selectively tensioning the first flexion wire 133, the second flexion wire 134, and the third flexion wire 135.

For example, the flexion actuator 132 may be installed on the user's hand or arm. For example, the flexion actuator 132 may be installed adjacent to the palm support 11. For example, the flexion actuator 132 may be positioned in a more proximal direction than the palm support 11 with respect to the user's arm. For example, the flexion actuator 132 may be installed on the user's wrist.

As another example, the flexion actuator 132 may be formed integrally with the palm support 11.

For example, the flexion actuator 132 may be a motor.

Meanwhile, the controller 17 may control (or operate) the flexion actuator 132 of the flexion assist unit 13 to perform the flexion of the finger wearing the flexion assist unit 13.

For example, the controller 17 may determine the posture and movement of the hand including the finger on the basis of information measured by the motion detection sensor 16. For example, the controller 17 may determine whether the user's finger performs the flexion or the extension on the basis of information measured by the motion detection sensor 16. For example, the controller 17 may determine whether the user performs a grip action or a grip releasing operation through the finger.

For example, the controller 17 may determine the posture and movement of the hand on the basis of the amount of displacement by which at least one of the first flexion wire 133, the second flexion wire 134, and the third flexion wire 135 moves, through an encoder provided in the flexion actuator 132.

For example, when the extension is not performed beyond a preset extension angle within a preset time from the start of the extension of the user's finger, the controller 17 may assist incomplete extension of the finger by driving the neural inhibition electrode 14.

For example, a time when the extension of the finger is started may be set to (i) a time when tension detected by a tension sensor connected to the extension assist unit 12 is reduced or (ii) a time when tension detected by a tension sensor connected to at least one of the first flexion wire 133, the second flexion wire 134, and the third flexion wire 135 is increased. In this case, the controller 17 may drive the neural inhibition electrode 14 on the basis of information detected by the tension sensors.

For example, a time when the extension of the finger is started may be set on the basis of a change in the angle of the finger joint, which is determined using information detected by the motion detection sensor 16.

For example, the controller 17 may calculate an external device (e.g., the flexion actuator 132) to calculate the tensile force of at least one of the first flexion wire 133, the second flexion wire 134, and the third flexion wire 135 for the finger flexion on the basis of the information measured by the motion detection sensor 16, and provide the calculated tensile force to at least one of the first flexion wire 133, the second flexion wire 134, and the third flexion wire 135.

In detail, the controller 17 may drive the external device (e.g., the flexion actuator 132) to provide the calculated tensile force to at least one of the first flexion wire 133, the second flexion wire 134, and the third flexion wire 135, thus individually controlling the angles of the metacarpophalangeal joint and the proximal joint of the finger and causing the finger to perform the flexion.

Furthermore, the controller 17 may calculate the tensile force for maintaining the finger flexion with the controlled individual angle on the basis of the information measured by the motion detection sensor 16, and drive the external device (e.g., the flexion actuator 132) according to the calculated tensile force, thus providing torque for maintaining the finger flexion to at least one of the first flexion wire 133, the second flexion wire 134, and the third flexion wire 135.

Meanwhile, it is to be noted that this is merely for an illustrative purpose, and other means known to those skilled in the art may be used.

For example, when the flexion is not performed beyond a preset flexion angle within a preset time from a time when the flexion of the finger is started in a gripping process through the user's finger, the controller 17 may drive the flexion assist unit 13 and/or the muscle excitation electrode 15, thus assisting the incomplete flexion of the finger.

For example, a time when the flexion of the finger is started may be set to (i) a time when tension detected by the tension sensor connected to at least one of the first flexion wire 133, the second flexion wire 134, and the third flexion wire 135 is reduced or (ii) a time when tension detected by the tension sensor connected to the extension assist unit 12 is increased. In this case, the controller 17 may drive the flexion assist unit 13 and/or the muscle excitation electrode 15 on the basis of the information detected by the tension sensors.

For example, the time when the flexion of the finger is started may be set on the basis of a change in angle of the finger joint determined using the information detected by the motion detection sensor 16. Meanwhile, it is to be noted that this is merely for an illustrative purpose, and other means known to those skilled in the art may be used.

Figure 4:
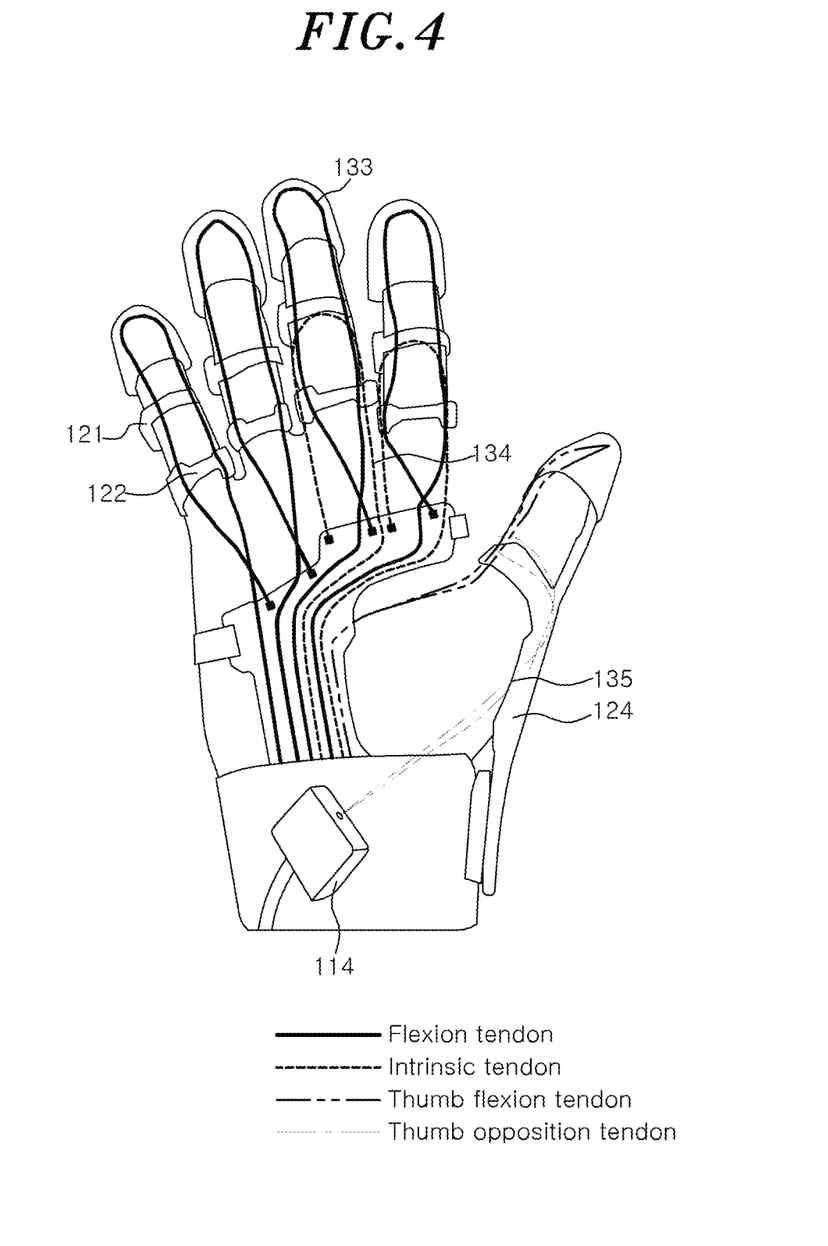
FIG. 4 describes a diagram illustrating an extension assist unit and a flexion assist unit in accordance with another embodiment.
Figure 5:
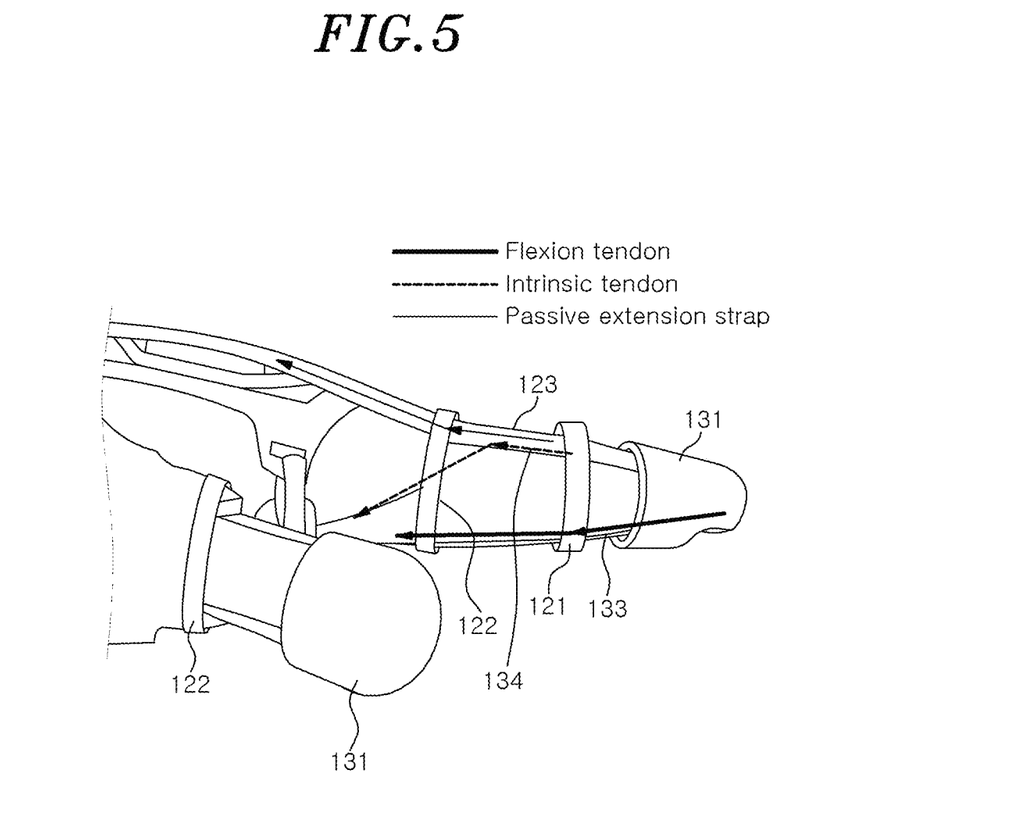
FIG. 5 depicts a diagram illustrating an index finger state in which an extension assist unit and a flexion assist unit in accordance with an embodiment are worn.

FIG. 4 describes a diagram illustrating an extension assist unit and a flexion assist unit in accordance with another embodiment, and FIG. 5 depicts a diagram illustrating an index finger state in which an extension assist unit and a flexion assist unit in accordance with an embodiment are worn.

Referring to FIGS. 4 to 5, the configuration of the palm support 11, the extension assist unit 12, and the flexion assist unit 13 in accordance with an embodiment may be checked.

The palm support 11 may be formed of a flexible material that is bendable, and may have the shape of a thin plane. For example, the palm support 11 may be formed of a silicone material. Thus, the palm support 11 may be bent according to the curved shape of the wrist or palm, and may surround at least a part of the palm. Although the drawings illustrate an embodiment where the palm support 11 surrounds only a part of the palm, the palm support 11 may be provided in the form of a glove which entirely surrounds the user's hand.

For example, the palm support 11 may be formed of a flexible polymer material, and be in close contact with the skin to provide frictional force sufficient to pull the wrist and the palm.

For example, the palm support 11 may include a hand-back support 111, a wrist support 112, and a plurality of coupling buttons 113.

The hand-back support 111 may be installed to surround the metacarpal region of fingers other than the thumb in a part of the user's palm.

The wrist support 112 may be installed to surround the periphery of the carpal region connecting the wrist and the lower part of the palm, namely, the wrist of the wrist region and the palm. For example, the hand-back support 111 and the wrist support 112 may be connected to each other.

The plurality of coupling buttons 113 may be disposed along the circumference of each of the hand-back support 111 and the wrist support 112.

For example, the plurality of coupling buttons 113 may be coupled to coupling holes 1221 formed in a first extension elastic member 123 or a second extension elastic member 124, which will be described later.

The extension assist unit 12 may be mounted at a first end thereof on the user's finger, and be mounted at a second end thereof on the palm support 11 to assist the extension of the finger equipped with the extension assist unit. For example, the extension assist unit 12 may be selectively mounted on the finger requiring the assistance of the extension, and be mounted on all five fingers.

For example, the extension assist unit 12 may include a first fixing ring 121, a second fixing ring 122, a first extension elastic member 123, and a second extension elastic member 124.

In an embodiment, in the extension assist unit 12 mounted on all the fingers, the first fixing rings 121 may be installed on all the fingers except for the thumb, the second fixing rings 122 and the first extension elastic members 123 may be installed on all the fingers, and the second extension elastic member 124 may be installed on only the thumb.

The first fixing ring 121 may be a ring-shaped member mounted on the middle phalanx region of the finger.

For example, when the extension assist unit 12 is mounted on the thumb, the first fixing ring 121 may not be mounted on the thumb. However, the present disclosure is not limited thereto.

The second fixing ring 122 may be a ring-shaped member mounted on the proximal phalange region of the finger.

The first extension elastic member 123 is an elastic member connected between the first fixing ring 121 and the palm support 11 or between the second fixing ring 122 and the palm support 11, and may assist the extension of the finger equipped with the first fixing ring 121 or the second fixing ring 122 through elastic force.

For example, the first extension elastic member 123 may be a member which is secured to the upper part of the first fixing ring 121 or the second fixing ring 122, namely, a part of the first fixing ring 121 or the second fixing ring 122 adjacent to the outside of the finger, and extends in the longitudinal direction of a corresponding finger.

The second extension elastic member 124 may be installed at only the thumb, and may be connected at a first end thereof to the outside part of the distal phalange support 131 and connected at a second end thereof to a part of the palm support 11 coming into contact with the wrist.

For example, the first extension elastic member 123 and the second extension elastic member 124 may be formed of silicone Si.

For example, the second extension elastic member 124 may be a member which is secured to the distal phalange support 133, is spaced apart from the first extension elastic member 123 at a predetermined angle, and extends in a longitudinal direction of a corresponding finger.

For example, the first extension elastic member 123 or the second extension elastic member 124 may be a strap type member having elasticity and flexibility.

For example, the first extension elastic member 123 or the second extension elastic member 124 may include coupling holes 1221 formed in a side extending from the first fixing ring 121 or the second fixing ring 122 to an opposite side.

The coupling hole 1221 may be fixedly coupled to the coupling button 113 protruding to the outside of the finger equipped with the first fixing ring 121 or the second fixing ring 122, among the plurality of coupling buttons 113 of the palm support 11.

For example, a plurality of coupling holes 1221 may be formed. In this case, the plurality of coupling holes 1221 may be formed to be spaced apart from each other in the longitudinal direction of the first extension elastic member 123 or the second extension elastic member 124. Thus, as the position of the coupling hole 1221 coupled to the coupling button 113 is adjusted, the tensile force of the extension elastic member 123 may be adjusted.

By the first extension elastic member 123 or the second extension elastic member 124, since the tensile force generated between (i) the middle phalanx region and (ii) the metacarpal or carpal region of the user is generated on the outside which is opposite to the inside toward which the finger is bent, the tensile force of the first extension elastic member 123 or the second extension elastic member 124 may provide a force for extending the user's finger.

For example, when the extension assist unit 12 is mounted on the thumb, the first extension elastic member 123 or the second extension elastic member 124 extending from the first fixing ring 121 or the second fixing ring 122 may extend in the longitudinal direction of the proximal phalange or the metacarpal of the thumb, on the outside of the finger, and then the coupling hole 1221 formed in the extended part may be coupled to one of the plurality of coupling buttons 113 formed on the wrist support 112.

For example, first coupling holes 1221 of the first extension elastic member 123 and the second extension elastic member 124 mounted on the thumb may be coupled to the coupling button 113 which is adjacent to the metacarpal region of the thumb and simultaneously is exposed to the outside of the thumb, among the plurality of coupling buttons 113 installed along the circumference of the wrist support 112.

For example, the first extension elastic member 123 or the second extension elastic member 124 mounted on the thumb may assist both the extension and the reposition of the thumb. In this case, as the position of the coupling button 113 coupled to the coupling hole 1221 of the first extension elastic member 123 or the second extension elastic member 124 is changed, the direction of the tensile force may be changed, and thereby the proportion of the extension and pronation due to the tensile force of the first extension elastic member 123 or the second extension elastic member 124 may be adjusted.

For example, when the extension assist unit 12 is mounted on fingers other than the thumb, the first extension elastic member 123 extending from the first fixing ring 121 extends in the longitudinal direction of the middle phalanx and proximal phalange of the finger, on the outside of the finger, and then the coupling hole 1221 formed in the extended part may be coupled to one of the plurality of coupling buttons 113 formed in the hand-back support 111.

In this case, the coupling hole 1221 may be secured to the coupling button 113 positioned on the outside of the metacarpal region of a corresponding finger, among the plurality of coupling buttons 113 installed along the circumference of the hand-back support 111.

The flexion assist unit 13 may assist the flexion of the finger due to the grip action of the hand. For example, the flexion assist unit 13 may include a distal phalange support 131, a first flexion wire 133, and a second flexion wire 134.

The distal phalange support 131 may be mounted on the end of the distal phalange region. For example, the distal phalange support 131 may have the shape of a thimble fitted over the end of the finger, as shown in FIGS. 4 to 5.

For example, the distal phalange support 131 may be formed of a flexible polymer material which is bendable. For example, the distal phalange support 131 may have frictional force to come into close contact with the skin and pull the distal phalange region of the finger.

The first flexion wire 133 may be a wire connected between the distal phalange support 131 and the controller 17. For example, as the first flexion wire 133 is tensioned by the controller 17, the distal phalange support 131 may be pulled to perform the flexion.

For example, the first flexion wire 133 may assist the flexion of all the fingers.

For example, after a first end of the first flexion wire 133 is fixed to a part of the distal phalange support 131 positioned on the inside of the finger, and a second end thereof extends in the longitudinal direction of the finger on the inside of the finger, the first flexion wire may be connected to the controller 17 which is disposed in a more proximal direction than the palm support 11.

Here, the first flexion wire 133 may be installed on all the fingers. When the first flexion wire 133 is mounted on the thumb, the first flexion wire 133 may be positioned on the opponens to face four fingers except for the thumb. For example, as the tensile force is supplied by the controller 17, the first flexion wire 133 may assist the flexion of the proximal inter-phalangeal joint or metacarpophalangeal joint of the finger.

The second flexion wire 134 may be a wire connected between the first fixing ring 121 or the second fixing ring 122 and the controller 17. For example, as the second flexion wire 134 is tensioned by the controller 17, it may assist the extension and flexion of some fingers. To be more specific, the second flexion wire 134 may be pulled to perform the flexion of the metacarpophalangeal joint of the finger and the extension of the proximal joint.

For example, as the tensile force is supplied by the controller 17, the second flexion wire 134 may assist the extension of the proximal inter-phalangeal joint of the finger and the flexion of the metacarpophalangeal joint.

For example, after the second flexion wire 134 is fixed to a part of the first extension elastic member 123 passing through the outside of the middle phalanx region of the finger and the second end thereof surrounds the circumference of the proximal phalange region of the finger obliquely inwards, the second flexion wire may be connected to the controller 17 which is disposed in a more proximal direction than the palm support 11.

Here, the second flexion wire 134 may be installed on the index finger and the middle finger except for the ring finger and the little finger.

The third flexion wire 135 may be installed on only the thumb, and be formed such that a first end thereof is secured to a wire holding device 114 installed on the palm support 11 and a second end thereof surrounds the metacarpophalangeal joint of the thumb and then passes through the wire holding device 114.

For example, each of the first flexion wire 133, the second flexion wire 134, and the third flexion wire 135 may be formed of an elastic material, so that the flexion of the finger can be smoothly performed. Furthermore, it is possible to prevent excessive tensile force from being supplied from the external device (e.g., the flexion actuator) by the excessive unintended output from the controller 17, thus preventing the flexion from being abruptly performed.

For example, each of the first flexion wire 133, the second flexion wire 134, and the third flexion wire 135 may be formed of a cable. For example, when both the extension assist unit 12 and the flexion assist unit 13 are mounted on one finger, the first flexion wire 133 extending from the distal phalange support 131 may be formed to pass through the inside part of each of the first and second fixing rings 121 and 122 which are mounted in a more proximal direction than the distal phalange support 131, and the second flexion wire 134 extending from a part of the first fixing ring 121 or the extension elastic member 123 passing through the outside of the middle phalanx region of the finger may be formed to pass through the inside part of the second fixing ring 122.

Through the above-described structure, when the finger performs the flexion and the extension, it is possible to prevent the first flexion wire 133, the second flexion wire 134, and the third flexion wire 135 from being removed from the finger, and the flexion of the finger joint may be sequentially performed according to the position of the joint.

For example, when the first flexion wire 133 is tensioned through the controller 17, the tensioned first flexion wire 133 may be primarily supported by the inside part of the first fixing ring 121, so that the tensile force may be applied to the distal phalange region prior to the proximal phalange region, and thereby the flexion may be performed in the order of the joints close to the distal phalange region.

Likewise, when the tensile force of the first flexion wire 133 is released, the order in which the flexion state of the joint is returned may also follow the order of joints adjacent to the distal phalange region.

Meanwhile, when the second flexion wire 134 is tensioned through the controller 17, the tensioned second flexion wire 134 may be primarily supported by the inside part of the second fixing ring 122, so that the tensile force may be first applied to the proximal phalange region, and thereby the flexion may be performed in the order of the joints close to the proximal phalange region.

Likewise, when the tensile force of the second flexion wire 134 is released, the order in which the flexion state of the joint is returned may also follow the order of joints adjacent to the proximal phalange region.

Meanwhile, when the third flexion wire 135 is tensioned through the controller 17, the tensioned third flexion wire 135 primarily surrounds the proximal phalange of the finger, so that the tensile force may be first applied to the proximal phalange region, and consequently the flexion may be performed in the order of the joints close to the proximal phalange region.

Likewise, when the tensile force of the third flexion wire 135 is released, the order in which the flexion state of the joint is returned may also follow the order of joints adjacent to the proximal phalange region.

As a result, it is possible to perform the natural movement of the finger during the flexion or extension of the hand through the extension assist unit 12 and the flexion assist unit 13.

For example, before the first flexion wire 133, the second flexion wire 134, and the third flexion wire 135 extend in the longitudinal direction of the finger to be connected to the controller 17, they may pass through the inside part of the palm support 11 as shown in FIG. 4.

Through the above-described structure, the palm support 11 may prevent the first flexion wire 133, the second flexion wire 134, and the third flexion wire 135 from being removed from the hand, and simultaneously guide a direction in which the tensile force of each of the first flexion wire 133, the second flexion wire 134, and the third flexion wire 135 is formed.

Meanwhile, the flexion assist unit may be mounted on all the five fingers. However, when the flexion assist unit 13 is mounted on all the five fingers, only the distal phalange support 131 and the first flexion wire 133 may be installed on the ring finger and the little finger, and no second flexion wire 134 and third flexion wire 135 may be installed thereon.

The reason is as follows: since the ring finger and the little finger is used relatively infrequently in everyday life, they may smoothly perform the flexion with only the first flexion wire 133. The second flexion wire 134 and the third flexion wire 135 connected to the controller 17 are not installed on the ring finger and the little finger, thus reducing complexity and cost.

Meanwhile, when the extension assist unit 12 and the flexion assist unit 13 are installed on all the five fingers, the finger motion assisting apparatus 1 in accordance with an embodiment of the present disclosure may include five first flexion wires 133, two second flexion wires 134, one third flexion wire 135, five first extension elastic members 123, and one second extension elastic member 124, but the present disclosure is not limited thereto.

Meanwhile, the finger motion assisting apparatus 1 in accordance with an embodiment of the present disclosure is configured such that the first extension elastic member 123, the second extension elastic member 124, the first flexion wire 133, and the third flexion wire 135 are formed on the thumb, so that it is possible to assist the flexion, pronation, and abduction of the opponens of the thumb, thus consequently assisting the extension and reposition of the thumb.

Furthermore, since the finger motion assisting apparatus 1 in accordance with an embodiment of the present disclosure does not include the external device (e.g., the flexion actuator) to which tensile force is supplied, the palm support 11, the extension assist unit 12, and the flexion assist unit 13 may be separated from the external device (e.g., the flexion actuator) to which tensile force is supplied.

The finger motion assisting apparatus 1 in accordance with an embodiment of the present disclosure selectively combines one or more modules among the extension assist unit and the flexion assist unit depending on the symptoms and conditions of patients, thus effectively assisting the movement of the hand.

The finger motion assisting apparatus 1 in accordance with another embodiment of the present disclosure selectively combines one or more modules among the extension assist unit 12, the flexion assist unit 13, the neural inhibition electrode 14, and the muscle excitation electrode 15 depending on the symptoms and conditions of patients, thus effectively assisting the movement of the hand.

Furthermore, it is possible to passively or actively assist rehabilitation training for patients with brain injury who suffer from hand paralysis after damage to a nervous system such as cerebral stroke or cerebral palsy.

Furthermore, it is possible to naturally stretch the finger which is bent due to stiffness, using a passive type extension assist unit.

Furthermore, it is possible to perform the flexion or extension of the thumb as well as the opposition for rotating the thumb to the inside of the palm or the reposition for restoring the finger from the rotated state, using the first extension elastic member 123, the second extension elastic member 124, the first flexion wire 133, and the third flexion wire 135.

Furthermore, it is possible to individually control the angles of the metacarpophalangeal joint and the proximal joint of the index finger and the middle finger, using the first extension elastic member 123, the first flexion wire 133, and the second flexion wire 134.

Furthermore, since the tensile force of the first flexion wire 133 or the second flexion wire 134 for the finger flexion is calculated and the first flexion wire 133 or the second flexion wire 134 is controlled according to the calculated tensile force, torque is provided according to the individual angle control of the metacarpophalangeal joint and the proximal joint of the index finger and the middle finger. Thus, as the angle and the torque are simultaneously controlled, the first flexion wire 133 or the second flexion wire 134 showing nonlinear characteristics due to friction and deformation is compensated for, so that the finger flexion can be rapidly and accurately assisted.

The above description is merely an exemplary description of the technical scope of the present disclosure, and it will be understood by those skilled in the art that various changes and modifications can be made without departing from original characteristics of the present disclosure. Therefore, the embodiments disclosed in the present disclosure are intended to explain, not to limit, the technical scope of the present disclosure, and the technical scope of the present disclosure is not limited by the embodiments. The protection scope of the present disclosure should be interpreted based on the following claims and it should be appreciated that all technical scopes included within a range equivalent thereto are included in the protection scope of the present disclosure.

What is claimed is:

1. An apparatus for assisting a finger motion, the apparatus comprising:
    a palm support installable to surround a part of a hand-back and a wrist;
    an extension assist unit securable at a first side thereof to a middle phalanx region of a finger and connected at a second side thereof to the palm support to assist extension of the finger through an elastic force between both ends; and
    a flexion assist unit comprising a distal phalange support mountable on an end of the finger, and a first flexion wire and a second flexion wire mountable on a part of the finger and assisting flexion of the finger on the basis of a tensile force provided to the flexion wires;
    wherein the extension assist unit further comprises a first extension elastic member connected at a first end thereof to an outside part of the distal phalange support and connected at a second end thereof to a part of the palm support coming into contact with the hand-back; and
    wherein the second flexion wire is formed such that a first end thereof is secured to a part of the first extension elastic member passing through an outside of the middle phalanx region of the finger, and a second end thereof is configured to surround a circumference of the proximal phalange region of the finger obliquely inwards and then passes through a part of the palm support coming into contact with the palm.

2. The apparatus of claim 1, wherein the first flexion wire assists the flexion of a first joint or a second joint of the finger, and
    the second flexion wire assists the extension of the first joint and assists the flexion of the second joint.

3. The apparatus of claim 1, wherein the first joint is a proximal inter-phalangeal joint of the finger, and
    the second joint is a metacarpophalangeal joint of the finger.

4. The apparatus of claim 1, wherein the extension assist unit comprises:
    a first fixing ring mountable on the middle phalanx region of the finger; and
    a second fixing ring mountable on a proximal phalange region of the finger.

5. The apparatus of claim 4, wherein the first flexion wire is formed such that a first end thereof is secured to an inside part of the distal phalange support and a second end thereof is configured to extend along a palm side of the finger and a part of the palm support coming into contact with the palm.

6. The apparatus of claim 4, wherein the extension assist unit further comprises a second extension elastic member which is connected at a first end thereof to an outside part of the distal phalange support and is connected at a second end thereof to a part of the palm support coming into contact with the wrist,
    the first fixing ring is installable on fingers other than a thumb,
    the second fixing ring and the first extension elastic member are installable on all fingers, and
    the second extension elastic member is installable on only the thumb.

7. The apparatus of claim 6, wherein the flexion assist unit further comprises a third flexion wire surrounding the metacarpophalangeal joint,
    the first flexion wire is installable on all the fingers,
    the second flexion wire is installable on only an index finger and a middle finger,
    the third flexion wire is installable on only the thumb, and is formed such that a first end thereof is secured to a wire holding device installed in the palm support and a second end thereof surrounds the metacarpophalangeal joint of the thumb and then passes through the wire holding device.

8. The apparatus of claim 6, wherein the palm support comprises:
    a hand-back support mountable to surround the metacarpal region in the palm;
    a wrist support mountable to surround a wrist region in the palm; and
    a plurality of coupling buttons disposed along circumferences of the hand-back support and the wrist support to be spaced apart from each other,
    wherein the first extension elastic member or the second extension elastic member comprises a coupling hole that may be coupled to any single coupling button among the plurality of coupling buttons.

9. The apparatus of claim 8, wherein, when the extension assist unit is mounted on the thumb, the second fixing ring is installed on the proximal phalange region, the coupling hole of the first extension elastic member is coupled to any one coupling button among the plurality of coupling buttons formed on the hand-back support, and the coupling hole of the second extension elastic member is coupled to any one coupling button among the plurality of coupling buttons formed on the wrist support, and when the extension assist unit is mounted on fingers other than the thumb, the first fixing ring is installed on the middle phalanx region, the second fixing ring is installed on the proximal phalange region, and the coupling hole of the first extension elastic member is coupled to any one coupling button among the plurality of coupling buttons formed on the hand-back support.

10. The apparatus of claim 4, wherein the first flexion wire passes through an inside part of each of the first and second fixing rings mountable on the finger equipped with the flexion assist unit, and the second flexion wire passes through the inside part of the second fixing ring mountable on the finger equipped with the flexion assist unit.

11. The apparatus of claim 6, wherein, when the flexion assist unit is mounted on the thumb, the flexion assist unit further comprises a metacarpal support mounted to surround the metacarpal region of the thumb, and the first flexion wire or the second flexion wire is formed to pass through the palm support after passing through an inside part of the metacarpal support.

12. The apparatus of claim 6, further comprising:

a motion detection sensor mountable on the finger or the palm to measure movement of a hand; and a controller calculating tensile force of at least one of the first flexion wire, the second flexion wire, and the third flexion wire for the finger flexion on the basis of information measured by the motion detection sensor, and controlling an external device to provide the calculated tensile force to at least one of the first flexion wire, the second flexion wire, and the third flexion wire.

13. The apparatus of claim 12, wherein the motion detection sensor comprises an inertia sensor to detect inertia of the finger or the palm region or a bending detection sensor to detect a joint motion of a finger region.

* * * * *